United States Patent [19]
Dubois et al.

[11] 4,228,087
[45] Oct. 14, 1980

[54] MESOGENIC PRODUCTS FOR LIQUID CRYSTAL CELLS

[75] Inventors: Jean C. Dubois; Francoise Barre, both of Paris, France

[73] Assignee: Thomson-CSF, Paris, France

[21] Appl. No.: 857,611

[22] Filed: Dec. 5, 1977

Related U.S. Application Data

[62] Division of Ser. No. 647,745, Jan. 7, 1976, Pat. No. 4,112,239.

[30] Foreign Application Priority Data

Jan. 10, 1975 [FR] France .................. 75 00719

[51] Int. Cl.² .......................... C09F 7/00; C11C 3/00
[52] U.S. Cl. ................................. 260/408; 560/141
[58] Field of Search ................... 260/408; 560/141

[56] References Cited

U.S. PATENT DOCUMENTS

| | | | |
|---|---|---|---|
| 2,141,172 | 12/1938 | Christiansen et al. | 560/141 |
| 2,457,805 | 1/1949 | Cade et al. | 260/408 X |
| 2,506,361 | 5/1950 | Higgins | 260/408 |
| 3,102,840 | 9/1963 | Musser et al. | 560/141 X |
| 3,334,125 | 8/1967 | Richter | 260/408 X |

OTHER PUBLICATIONS

Chemical Abstracts 42 1919c (1948).

*Primary Examiner*—Helen M. S. Sneed
*Attorney, Agent, or Firm*—Oblon, Fisher, Spivak, McClelland & Maier

[57] ABSTRACT

The present invention relates to a family of substances which, in different temperature ranges, exhibit smectic or nematic properties of mesomorphism. Their general formula is:

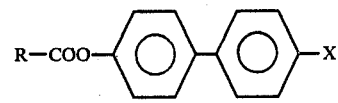

where R designates one of the three radicals:

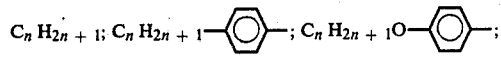

(n being a whole number ranging from 1 to 20) and X designating a halogen (Br preferably) or the nitrile radical C N.

3 Claims, No Drawings

MESOGENIC PRODUCTS FOR LIQUID CRYSTAL CELLS

This is a division of application Ser. No. 647,745, filed Jan. 7, 1976, now U.S. Pat. No. 4,112,239.

The present invention relates to mesogenic products comprising a substance or a mixture of substances which, within a certain temperature range, exhibit a mesomorphic phase, characteristic of a liquid crystal.

The possible applications in display cells, of various liquid crystals, depends upon the nature of their mesomorphism (nematic or smectic in particular), the extent of their temperature range, and different factors such as dielectric anisotropy, coloration and stability.

The mesogenic products in accordance with the invention are stable, colorless, and have a positive dielectric anisotropy in excess of 5. By mixing, it is possible to widen and narrow the temperature range exhibited by the substances in the pure state.

According to the invention, there is provided mesogenic products of the general formula:

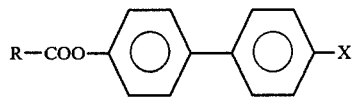
(1)

wherein R belongs to the group of the following three radicals:

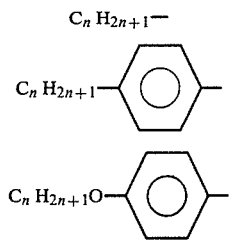

where n is a whole number ranging between 1 and 20; and wherein X belongs to the following group: a halogen and the nitrile radical (C N).

A method of manufacturing those products is as follows:

First case: X=Br or Cl

A parabenzophenol ester of the formula:

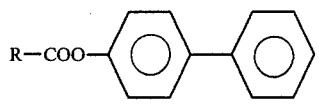
(2)

where R is one of the aforesaid radicals, is bromated (or chlorinated). An ester of this kind itself has been previously obtained in a manner known per se for example by reacting organic acid chloride containing the radical, with parabenzophenol.

In the case of bromide, the parabenzophenol ester reacts at ambient temperature when liquid bromide is poured into a solution of ester and acetic acid. The bromating efficiency is of the order of 50% and yields a compound of the formula:

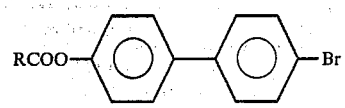
(3)

Second case: X=C N

In a first stage, the operation described in the first case is performed, yielding the compound formula (3).

In a second stage, the bromide is replaced by the nitrile group in the compound of formula (3). For this purpose, the latter is reacted at 200° C. with cuprous cyanide in the liquid phase (dimethyl formamide).

Example of the first case: $X=Br$ and $R=C_8H_{17}$

Using a known method, a quantity of parabenzophenol nonanoate is prepared:

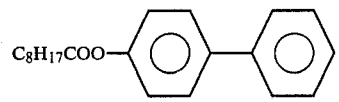

representing 0.06 mols, this being dissolved in a mixture containing 32 milliliters of acetic acid and 16 milliliters of acetic anhydride, in which a small iodine crystal (for example one tenth of a gram) has previously been dissolved. Then at 35° C., a quantity of bromide representing 0.18 mols is poured slowly in. The reaction is allowed to take place for twelve hours at ambient temperature. The precipitate form is filtered off, rinsed in acetic acid and then water. The liquors are concentrated by evaporation using heating, and then refiltered. The precipitates are filtered and recrystallised in ethanol. In this way, 0.35 mols of p'-benzophenol-p-bromononanoate are obtained.

Example of the second case: $X=C N$ and $R=C_8H_{17}$

Using the method described in the previous example, a certain quantity of p'-benzophenol-p-bromo-nonanoate is prepared, 0.025 mols of which are dissolved in a solution containing 0.03 mols of cuprous cyanide in 14 milliliters of dimethylforamide. The reaction is allowed to take place at 200° C. for six hours. Following this, the solution is poured into a mixture containing 25% of ethylene diamine and 75% of water. The product is extracted using ether and then purified by a chromatographic technique on a silica column. The result is 0.008 mols of p'-benzophenol-p-nitrile nonanoate.

The following table sets out the mesomorphism observed in respect of a number of substances specified by the radical X and the radical R contained in the general formula (1):

| Radical X | Radical R | Mesomorphism observed |
|---|---|---|
| Br | C₄H₉O—⟨O⟩— | smectic from 148° C. to 230° C. |
| Br | C₇H₁₅—⟨O⟩— | smectic from 133° C. to 194° C. nematic from 194° C. to 200° C. |
| Br CN | C₈H₁₇  C₇H₁₅—⟨O⟩— | smectic from 65° C. to 100° C. nematic from 95.5° C. to 230° C. (dielectric anisotropy : +8) |

| Radical X | Radical R | Mesomorphism observed |
|---|---|---|
| CN | $C_4H_9O-\bigcirc-$ | nematic from 120° C. to 270° C. (dielectric anisotropy : +8) |
| CN | $C_5H_{11}$ | nematic from 56° C. to 72° C. (dielectric anisotropy : +10) |
| CN | $C_7H_{15}$ | nematic by supercooling below 78° C. (dielectric anisotropy : +10) |
| CN | $C_8H_{17}$ | smectic from 26° or 43.5° to 58° C. nematic from 58° C. to 76° C. |

Mixtures of the different substances of formula (1), either between one another or with other liquid crystals, make it possible to vary the mesomorphic range.

By way of example, take the following substances:

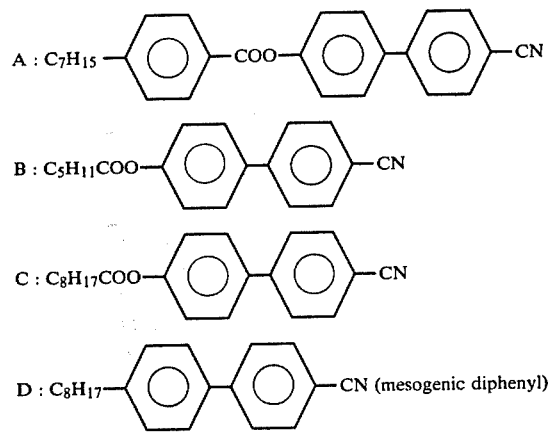

in respect of which the following results have been observed:

| Composition of the mixture (in fractions of mols) | Observed mesomorphism |
|---|---|
| ⅓ A + ⅓ B + ⅓ C | nematic from 24° to 94° C. |
| ½ A + ½ B | nematic from 38° C. to 111° C. |
| ½ C + ½ D | smectic (A) from 12° C. to 46° C. nematic from 46° C. to 53° C. |

What we claim is:

1. A mesogenic compound of the formula:

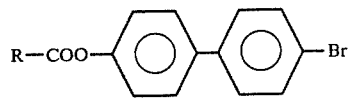

wherein R is $C_nH_{2n+1}-$; and n is a whole number from 1 to 20.

2. A mesogenic compound of the formula:

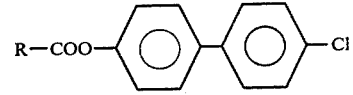

wherein R is $C_nH_{2n+1}-$; and n is a whole number from 1 to 20.

3. A mesogenic compound of the formula:

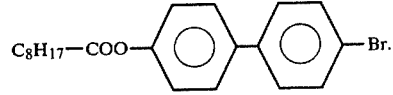

* * * * *